United States Patent
Jackson et al.

(10) Patent No.: US 6,936,171 B2
(45) Date of Patent: Aug. 30, 2005

(54) PROCESS FOR CATALYST RECOVERY FROM HYDROCYANATION PRODUCT MIXTURES

(75) Inventors: Scott C. Jackson, Wilmington, DE (US); Ronald J. Mckinney, Wilmington, DE (US)

(73) Assignee: Invista North America S.a.r.l., Wilmington, DE (US)

( * ) Notice: Subject to any disclaimer, the term of this patent is extended or adjusted under 35 U.S.C. 154(b) by 170 days.

(21) Appl. No.: 10/338,567

(22) Filed: Jan. 8, 2003

(65) Prior Publication Data

US 2004/0140263 A1 Jul. 22, 2004

(51) Int. Cl.$^7$ .............................................. B01D 11/00
(52) U.S. Cl. ...................... 210/634; 210/636; 210/639; 558/335; 558/338
(58) Field of Search ................................ 210/634, 638, 210/639; 558/332–340, 360–364; 568/454

(56) References Cited

U.S. PATENT DOCUMENTS

| | | |
|---|---|---|
| 3,496,215 A | 2/1970 | Drinkard et al. |
| 3,496,217 A | 2/1970 | Drinkard, Jr. et al. |
| 3,496,218 A | 2/1970 | Drinkard, Jr. et al. |
| 3,766,241 A | 10/1973 | Drinkard, Jr. |
| 3,773,609 A | 11/1973 | Walter |
| 5,512,695 A | 4/1996 | Kreutzer et al. |
| 5,512,696 A | 4/1996 | Kreutzer et al. |
| 5,523,453 A | 6/1996 | Breikss |
| 5,543,536 A | 8/1996 | Tam |
| 5,663,369 A | 9/1997 | Kreutzer et al. |
| 5,688,986 A | 11/1997 | Tam et al. |
| 5,693,843 A | 12/1997 | Breikss et al. |
| 5,723,641 A | 3/1998 | Tam et al. |
| 5,847,191 A | 12/1998 | Bunel et al. |
| 5,959,135 A | 9/1999 | Garner et al. |
| 6,048,996 A * | 4/2000 | Clarkson et al. ............ 558/338 |
| 6,120,700 A | 9/2000 | Foo et al. |
| 6,171,996 B1 | 1/2001 | Garner et al. |
| 6,171,997 B1 | 1/2001 | Foo et al. |
| 6,399,534 B2 | 6/2002 | Bunel et al. |
| 6,660,876 B2 * | 12/2003 | Gagne et al. ............... 558/156 |

FOREIGN PATENT DOCUMENTS

WO     0136429     5/2000

* cited by examiner

*Primary Examiner*—Joseph Drodge

(57) ABSTRACT

Disclosed herein is a process for recovering diphosphite-containing compounds from a mixture comprising diphosphite-containing compounds and organic dinitriles and Lewis acid, using liquid-liquid extraction, wherein the molar ratio of organic mononitrile present to organic dinitrile from about 0.01 to about 2.5 and wherein the mixtured is treated with a Lewis base compound selected from the group consisting of monodentate phosphite ligand, alcohol, water, organoamines, ammonia and basic resin, and wherein the extraction solvent is a saturated or unsaturated alkane or saturated or unsaturated cycloalkane; wherein the Lewis base compound is selected from the group consisting of water, methanol, ethanol, isopropanol, ethylene glycol, phenol, cresol, or xylenol. Also disclosed are pre-treatments to enhance extractability of the diphosphite-containing compounds.

12 Claims, No Drawings

PROCESS FOR CATALYST RECOVERY FROM HYDROCYANATION PRODUCT MIXTURES

FIELD OF THE INVENTION

The invention relates to recovery of catalyst and ligand from a hydrocyanation reaction product mixture comprising organic dinitriles using liquid-liquid extraction.

BACKGROUND OF THE INVENTION

It is well known in the art that complexes of nickel with phosphorous-containing ligands are useful as catalysts in hydrocyanation reactions. Such nickel complexes using monodentate phosphites are known to catalyze hydrocyanation of butadiene to produce a mixture of pentenenitriles. These catalysts are also useful in the subsequent hydrocyanation of pentenenitriles to produce adiponitrile, an important intermediate in the production of nylon. It is further known that bidentate phoshite and phosphinite ligands can be used to form nickel-based catalysts to perform such hydrocyanation reactions.

U.S. Pat. No. 3,773,809 describes a process for the recovery of Ni complexes of organic phosphites from a product fluid containing organic nitriles produced by hydrocyanating an ethylenically unsaturated organic mononitrile such as 3-pentenenitrile through extraction of the product fluid with a paraffin or cycloparaffin hydrocarbon solvent. It describes that the ratio of mononitrile to dinitrile must be 0.65 or less to obtain effective recovery, with efficiency improving as the ratio is reduced. Therefore, when hydrocyanation reaction conditions produces a mononitrile to dintrile ratio greater than 0.65, mononitrile must be removed from the product mixture before extraction is performed.

In contrast to the recovery of catalyst comprising monodentate phosphites and Ni, we have observed that Lewis acids utilized as promoters in the hydrocyanation reaction inhibit the effective recovery of diphosphite-nickel catalysts. It is therefore desirable to find conditions underwhich this inhibiting effect is reduced or eliminated.

There is a desire to provide better methods for recovering Ni diphosphite complexes in such a manner that minimal equipment and additional extraction solvent is required.

It is another object of this invention to be able to recover the complexes and operate the extraction in such a way that there is a broad composition range of the reactor product from which the catalyst is to be recovered. A further object of the invention is to delineate operating conditions whereby economical recovery of the catalyst is feasible.

Further objects, features, and advantages of the invention will become apparent from the detailed description that follows.

SUMMARY OF THE INVENTION

Disclosed herein is a process for recovering diphosphite-containing compounds from a mixture comprising diphosphite-containing compounds and organic mononitriles and organic dinitriles, using liquid-liquid extraction, wherein the molar ratio of organic mononitrile present to organic dinitrile is from about 0.65 to about 2.5 and wherein the extraction solvent is a saturated or unsaturated alkane or saturated or unsaturated cycloalkane.

Also disclosed is a process for recovering diphosphite-containing compounds from a mixture comprising diphosphite-containing compounds and organic dinitriles and Lewis acid, using liquid-liquid extraction, wherein the molar ratio of organic mononitrile present to organic dinitrile is from about 0.01 to about 2.5 and wherein the mixture is treated with a Lewis base compound selected from the group consisting of monodentate phosphite ligand, alcohol, water, organoamines, ammonia, and basic resin, and wherein the extraction solvent is a saturated or unsaturated alkane or saturated or unsaturated cycloalkane.

DETAILED DESCRIPTION OF THE INVENTION

The processes of the present invention involve methods for recovering diphosphite-containing compounds from a mixture comprising diphosphite-containing compounds and organic dinitriles, using liquid-liquid extraction. We have discovered that catalysts comprising diphosphite complexes of Ni allow recovery via liquid-liquid extraction to occur at a higher ratio of organic mono-nitrile to organic dinitrile than described in U.S. Pat. No. 3,773,809. Though extraction efficiency is still maximized as the mononitrile to dinitrile ratio is reduced, we have successfully demonstrated catalyst recovery at mononitrile to dinitrile ratios as high as 2.3, which is significantly higher than that reported in U.S. Pat. No. 3,773,809. Consequently, under hydrocyanation reaction conditions that produce mononitrile to dinitrile ratios of greater than 0.65, the unreacted mononitriles do not have to be removed before extraction in order to recover the catalyst, resulting in a processing advantage. The preferred mononitrile to dinitrile ratio range is 0.01 to 2.5. The most preferred range is 0.01 to 1.5.

We have also discovered that the inhibiting effect of Lewis acids on the recovery of diphosphite-nickel catalysts via liquid-liquid extraction is reduced by increasing the temperature during extraction. Maximum temperature is limited by the volatility of the hydrocarbon solvent utilized, but we have found recovery improves as the temperature is increased. The preferred operating range is 40° C. to 100° C. The most preferred range is 50° C. to 80° C.

We have also discovered that inhibiting effect of Lewis acids on the recovery of diphosphite-nickel catalysts via liquid-liquid extraction is reduced by introducing Lewis base compounds to the catalyst-containing mixture which apparently bind either to the nickel catalyst or to the Lewis acid and disrupt the association of the Lewis acid with the catalyst. We have found that introducing monodentate phosphites to the catalyst mixture can improve the extraction recovery. If the size of these monodentate phosphites become large, this effect is reduced. Some of the monophosphite ligands that are useful as an extraction enhancement treatment are those which are disclosed in Drinkard et al U.S. Pat. No. 3,496,215, U.S. Pat. No. 3,496,217, U.S. Pat. No. 3,496,218, U.S. Pat. No. 5,543,536, and BASF WO 01/36429.

We have found that the addition of weakly Lewis basic compounds, such as water or alcohols, or more strongly Lewis basic compounds such as ammonia, aryl- or alkyl amines, such as pyridine or triethylamine, or basic resins such as Amberlyst 21®, a commercially available basic resin made by Rohm and Haas, can reduce or eliminate the inhibiting effect of Lewis acid on catalyst recovery.

The process may be carried out for the recovery of various bidentate phosphorus-containing ligands and nickel complex catalysts thereof.

Suitable ligands for the present invention are bidentate phosphorous-containing ligands selected from the group consisting of bidentate phosphites, and bidentate phosphinites. Preferred ligands are bidentate phosphite ligands.

The preferred bidentate phosphite ligands are of the following structural formulae:

$(R^1O)_2P(OZO)P(OR^1)_2$,  I

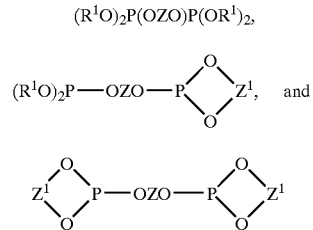
II

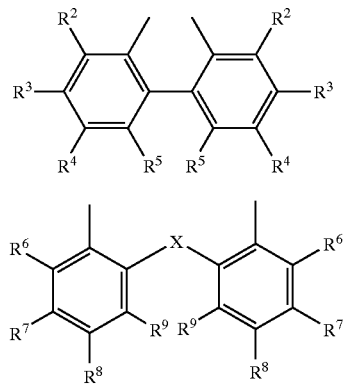
III wherein in I, II and III $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae IV, V, VI, VII, and VIII:

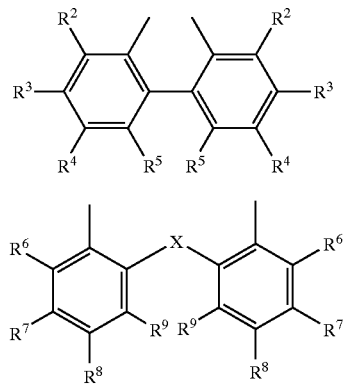

IV

V and wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy; X is O, S, or $CH(R^{10})$;
$R^{10}$ is H or $C_1$ to $C_{12}$ alkyl;

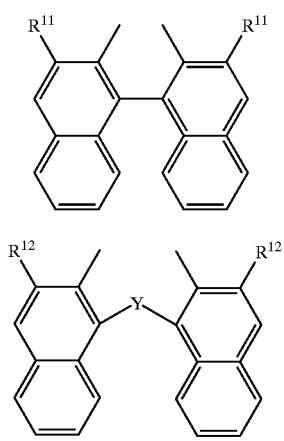

VI

VII and wherein
$R^{11}$ and $R^{12}$ are independently selected from the group consisting of
H, $C_1$ to $C_{12}$ alkyl, and $C_1$ to $C_{12}$ alkoxy; and $CO_2R^{13}$,
$R^{13}$ is $C_1$ to $C_{12}$ alkyl or $C_6$ to $C_{10}$ aryl, unsubstituted or substituted with $C_1$ to $C_4$ alkyl;

Y is O, S, or $CH(R^{14})$;
$R^{14}$ is H or $C_1$ to $C_{12}$ alkyl;

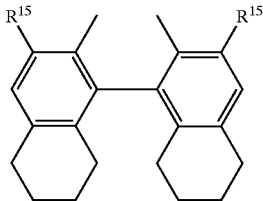

VIII wherein $R^{15}$ is selected from the group consisting of H, $C_1$ to $C_{12}$ alkyl, and
$C_1$ to $C_{12}$ alkoxy and $CO_2R^{16}$;
$R^{16}$ is $C_1$ to $C_{12}$ alkyl or $C_6$ to $C_{10}$ aryl, unsubstituted or substituted with $C_1$ to $C_4$ alkyl.

In the structural formulae I through VIII, the $C_1$ to $C_{12}$ alkyl, and $C_1$ to $C_{12}$ alkoxy groups may be straight chain or branched.

Examples of bidentate phosphite ligands that are useful in the present process include those having the formulae IX to XXXII, shown below wherein for each formula, $R^{17}$ is selected from the group consisting of methyl, ethyl or isopropyl, and $R^{18}$ and $R^{19}$ are independently selected from H or methyl:

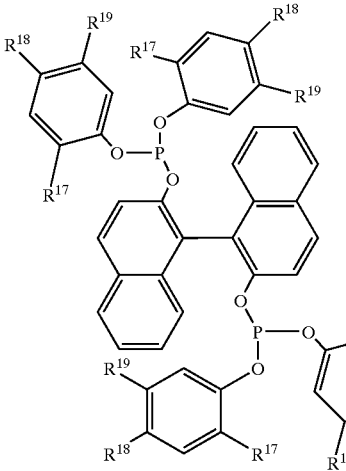

IX

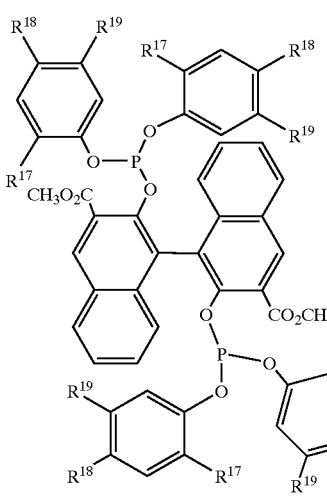

X

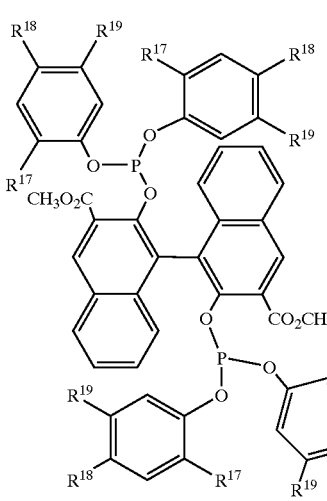

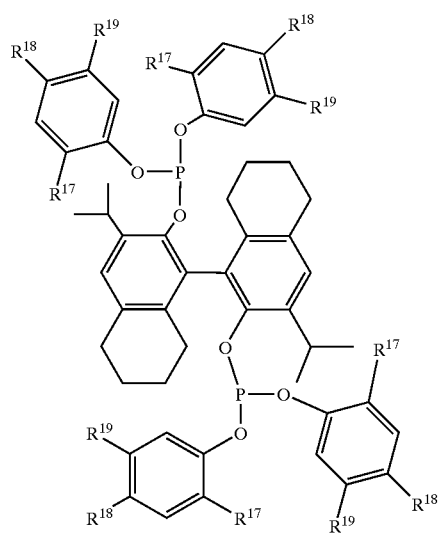
XI
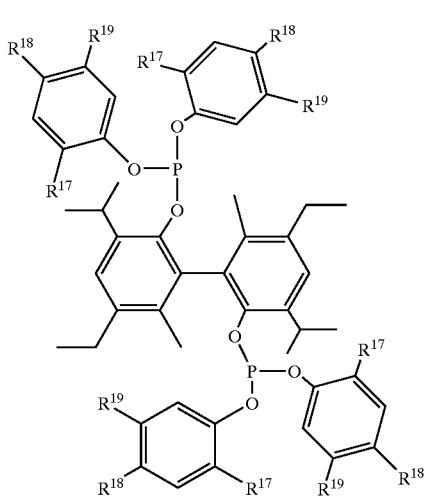
XIV
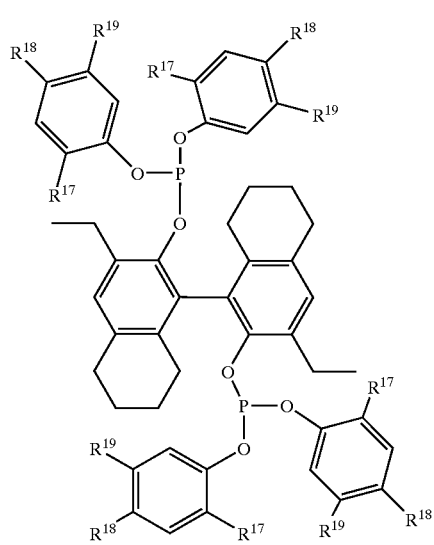
XII
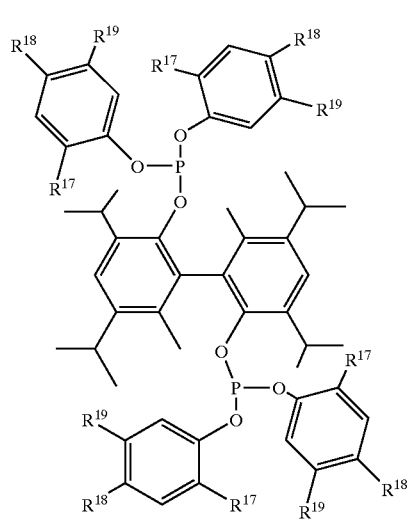
XV
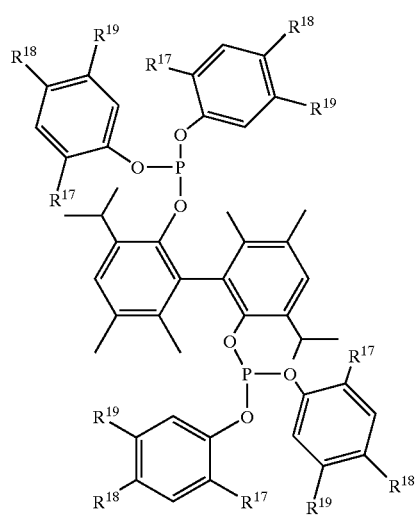
XIII
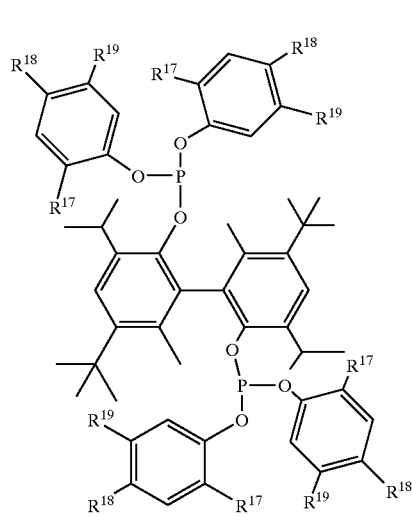
XVI

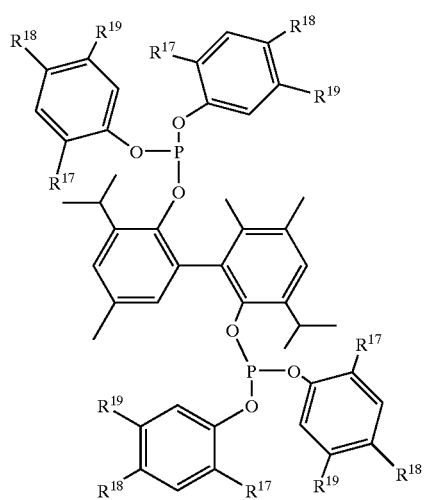
XVII
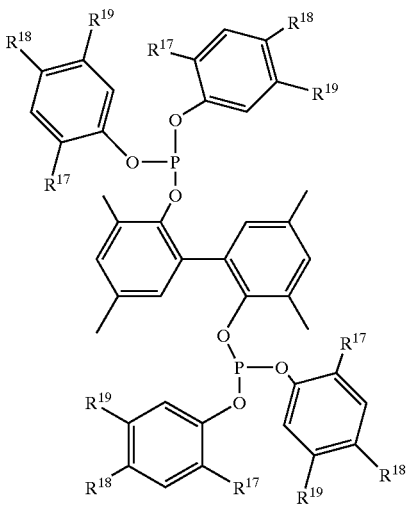
XX
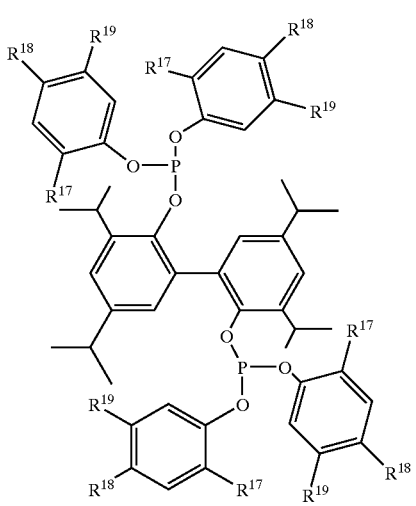
XVIII
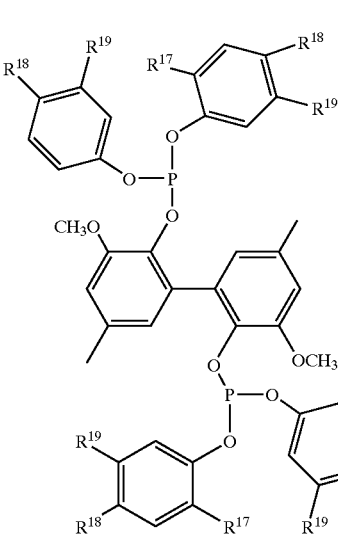
XXI
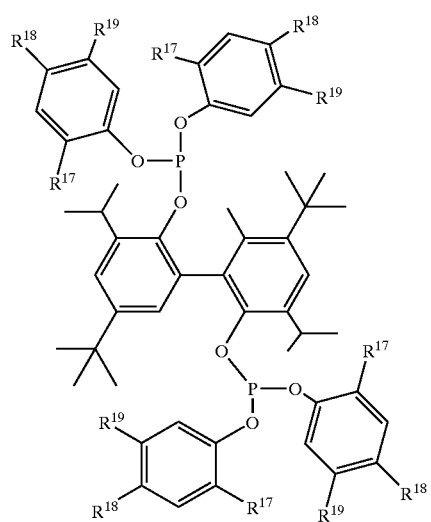
XIX
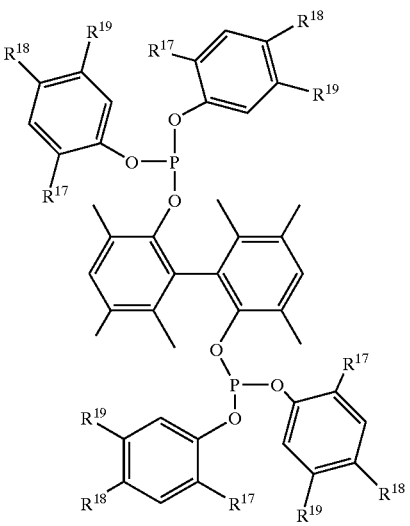
XXII

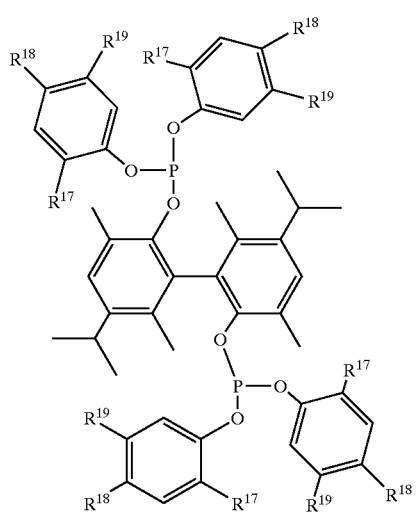
XXIII
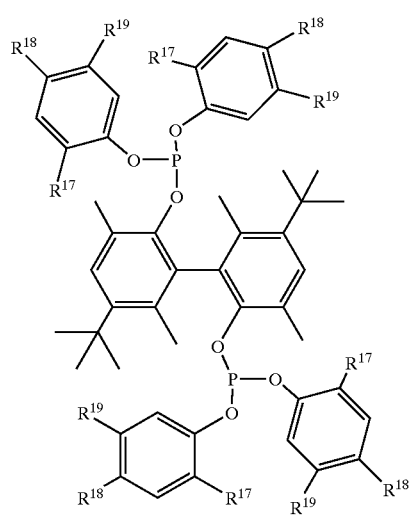
XXIV
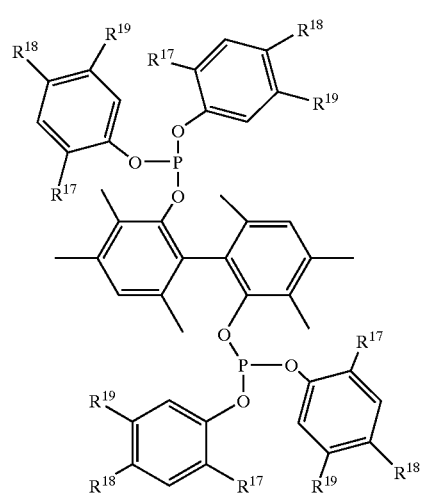
XXV
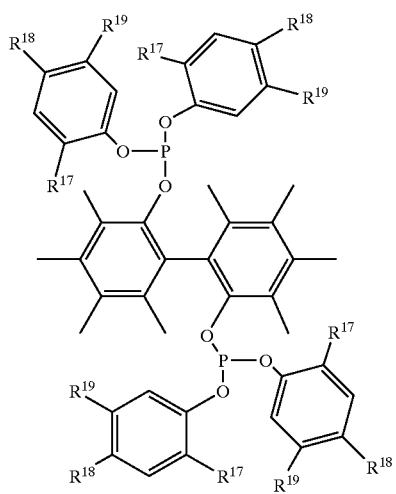
XXVI
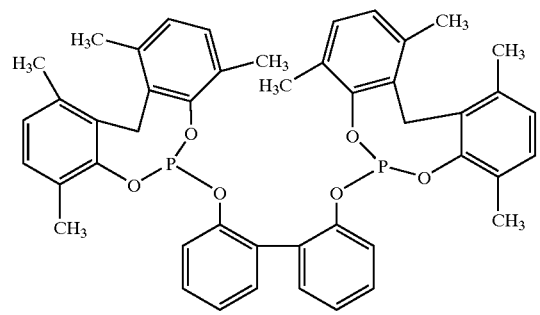
XXVII
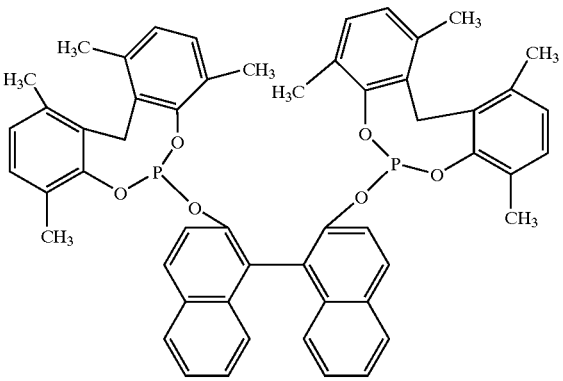
XXVIII
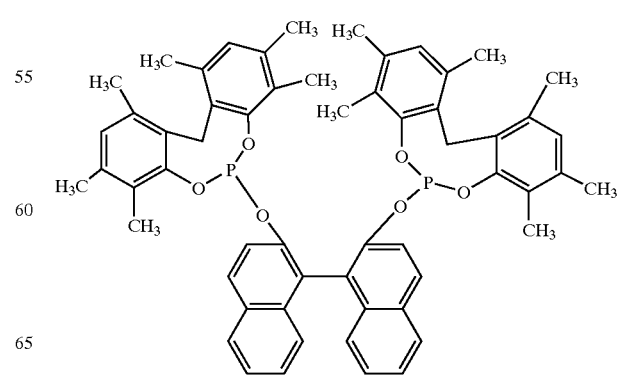
XXIX

XXX

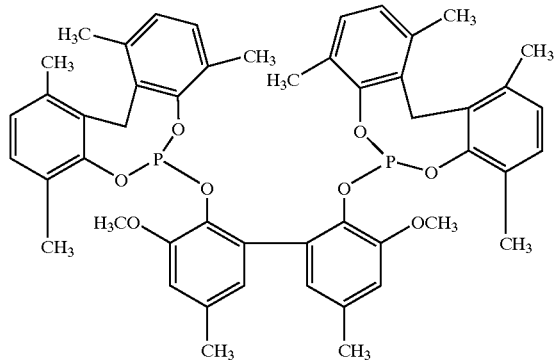

XXXI

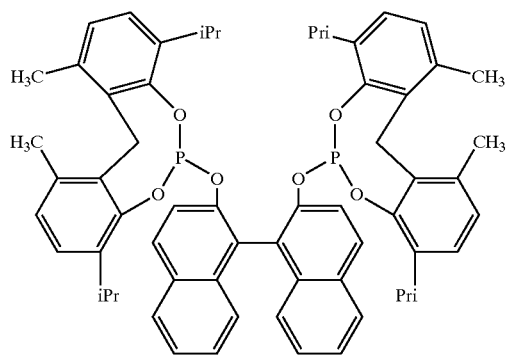

XXXII

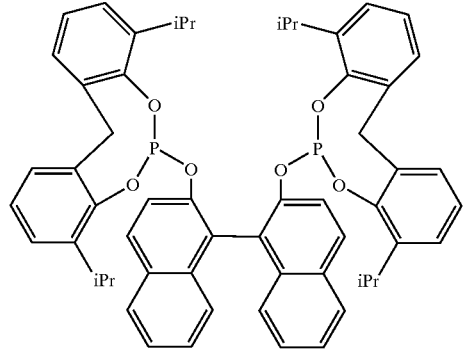

Additional suitable bidentate phosphites are of the type disclosed in U.S. Pat. Nos. 5,512,695; 5,512,696; 5,663,369; 5,688,986; 5,723,641; 5,847,191; 5,959,135; 6,120,700; 6,171,996; 6,171,997; 6,399,534; the disclosures of which are incorporated herein by reference. Suitable bidentate phosphinites are of the type disclosed in U.S. Pat. Nos. 5,523,453 and 5,693,843, the disclosures of which are incorporated herein by reference.

With one or a combination of these treatments, it is possible to recover the catalyst more efficiently with fewer stages of extraction. This is a great benefit in that it adds flexibility to the process and reduces process costs. With these treatments, the extraction can be done in a smaller extraction column, or in simple mixer settlers and/or the extraction can be accomplished using far less solvent than previously reported. The extraction can be accomplished across a broad range of compositions. To be most effective, these treatments should be done before extraction.

The present invention has advantages over prior methods for recovering of phosphite and diphosphite Ni complexes that are used as catalysts. These advantages include the ability to achieve a very high fractional recovery; the ability to achieve economical recovery in simple equipment, such as mixer-settlers instead of more complicated extraction towers; the ability to perform the extraction over a wider range of hydrocyanation reaction compositions; and the ability to enhance the extraction to significantly increase the recoverability of the catalyst in various types of extraction-suitable vessels.

The present invention also pertains to an economical method for recovering phosphite and Ni diphosphite complexes from a hydrocyanation reaction product mixture comprised of organic dinitriles using liquid-liquid extraction.

EXAMPLES

In the following examples, values for extraction coefficient are the ratio of weight fraction of catalyst in the extract (hydrocarbon phase) versus the weight fraction of catalyst in the raffinate (organonitrile phase). An increase in extraction coefficient results in greater efficiency in recovering catalyst.

Examples 1–5

These examples illustrate that effective catalyst recovery occurs for a mononitrile to dinitrile ratio greater than 0.65

Five different mixtures comprised of a Ni diphosphite complex, with the diphosphite ligand shown in Structure IX (where R17 is isopropyl, R18 is H, and R19 is methyl), $ZnCl_2$ (equimolar with Ni) and differing in the ratio or mononitrile to dinitrile, were separately liquid-liquid batch extracted with an equal weight of cyane. The molar ratio of organic mononitrile to organic dinitrile and the resulting extraction coefficients are shown in the Table 1 below. A compound may be effectively recovered if it has an extraction coefficient of 1 or greater at solvent to feed ratios greater than 1 using a countercurrent multistage extractor.

TABLE 1

Catalyst and ligand extraction coefficient for various ratios of mononitriles to dinitriles.

| Example | mononitrile/ dinitrile | Catalyst extraction coefficient | ligand extraction coefficient |
| --- | --- | --- | --- |
| 1 | 2.33 | 1.28 | 4.09 |
| 2 | 1.85 | 1.33 | 8.08 |
| 3 | 1.19 | 2.02 | 16.97 |
| 4 | 0.91 | 2.63 | 35.99 |
| 5 | 0.57 | 4.82 | 49.59 |

Examples 6 and 7 show that increasing temperature allows more effective catalyst recovery at limited holdup time.

Example 6

Effect of Temperature on the Extractability of the Diphosphite Ligand Catalyst

A mixture comprised predominantly of organic dinitriles and a Ni diphosphite complex, the structure of the diphosphite ligand being shown in Structure IX (where R17 is isopropyl, R18 is H, and R19 is methyl) and $ZnCl_2$ (equimolar with Ni) was divided into two portions. One portion was batch liquid-liquid extracted at 40° C., and the other at 50° C., with an equal weight of cyclohexane. Both portions were sampled with time and the progress of the catalyst recovery into the extract phase is shown in Table 2 as the percent of the final steady state value achieved at a given time.

TABLE 2

Concentration at Diphosphite ligand with time in the extracting solvent phase.

| Time, minutes | % of steady state concentration at 40° C. | % of steady state concentration at 50° C. |
|---|---|---|
| 2 | 12 | 11 |
| 4 | 19 | 38 |
| 8 | 34 | 53 |
| 14 | 52 | 95 |
| 30 | 78 | 104 |
| 60 | 100 | 102 |
| 91 | 100 | 100 |

Example 7

Effect of Temperature on the Extractability on Catalyst

A mixture comprised predominantly of organic dinitriles and a Ni diphosphite complex, the structure of the diphosphite ligand being shown in Structure XIII (where R17 is methyl, R18 is methyl and R19 is H) and $ZnCl_2$ (equimolar with Ni) was divided into three portions. The portions were batch liquid-liquid extracted at 50° C., 65° C. and 80° C., respectively, with an equal weight of n-octane and monitored with time. The results are shown in Table 3.

TABLE 3

| Time | % of steady state at 50° C. | % of steady state at 65° C. | % of steady state at 80° C. |
|---|---|---|---|
| 2 | 0.0 | 0.0 | 1.8 |
| 4 | 0.0 | 0.0 | 1.6 |
| 8 | 0.0 | 0.0 | 3.6 |
| 14 | 0.0 | 0.0 | 4.3 |
| 20 | 0.0 | 0.0 | 3.6 |
| 30 | 0.0 | 0.0 | 7.6 |
| 60 | 0.0 | 1.6 | 16.3 |
| 90 | 0.7 | 4.0 | 48.6 |

Example 8

Effect of Adding Water

Fifteen grams of a mixture comprised predominantly of organic dinitriles and a Ni diphosphite complex, the structure of the diphosphite ligand being shown in Structure XIII (where R17 is methyl, R18 is methyl and R19 is H) and $ZnCl_2$ (equimolar with Ni), was batch liquid-liquid extracted at a temperature of 50° C. with an equal weight of cyclohexane for one hour resulting in an catalyst extraction coefficient of 4.3. To this mixture, 100 microliters of water was added. After continuing to heat and agitate for another hour, the diphosphite Ni extraction coefficient was measured as 13.4—a three fold increase.

Examples 9–20

Effect of Addition of Organic Monophosphite Compounds

Examples 9–20 illustrate the beneficial impact on catalyst recovery of adding a monophosphite to the catalyst mixture. They utilize a common experimental protocol as follows: A mixture comprised pentenenitrile and adiponitrile (in a ratio of 0.3) and a Ni diphosphite complex (2–5 wt %) and $ZnCl_2$ (equimolar with Ni) and very small amounts (<0.3 wt %) of monophosphites (present as side products of the ligand synthesis) was divided into three portions. Different monophosphites were added to the second and third portion in each example as shown in Table 4 to bring the monophosphite concentration up to 5 wt %. Each portion was batch extracted with an equal weight of cyclohexane at 50° C. for 30 minutes and then allowed to cool to 25° C. for one hour and sampled at room temperature. The measured catalyst extraction coefficients are shown in Table 4.

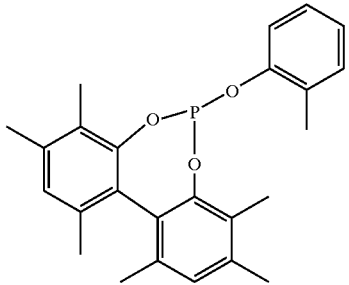

XXXIII

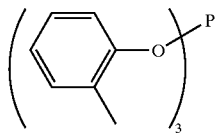

XXXIV

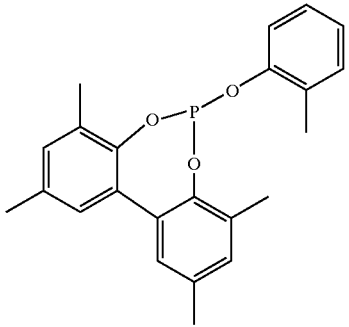

XXXV

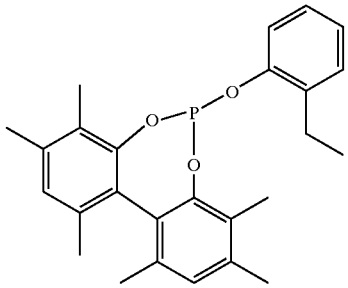

XXXVI

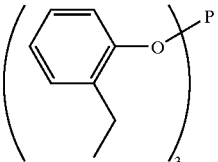

XXXVII

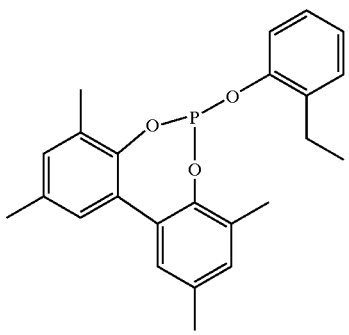

XXXVIII

TABLE 4

| Example | Ligand | $R^{17}$ | $R^{18}$ | $R^{19}$ | Additive | Extraction coefficient |
|---|---|---|---|---|---|---|
| 9 | XXV | methyl | H | H | none | 0.9 |
| 10 | XXV | methyl | H | H | XXXIII | 9.2 |
| 11 | XXV | methyl | H | H | XXXIV | 12.8 |
| 12 | XX | methyl | H | H | none | 0.3 |
| 13 | XX | methyl | H | H | XXXV | 2.4 |
| 14 | XX | methyl | H | H | XXXIV | 3.9 |
| 15 | XXV | ethyl | H | H | none | 4.7 |
| 16 | XXV | ethyl | H | H | XXXVI | >10 |
| 17 | XXV | ethyl | H | H | XXXVII | >10 |
| 18 | XX | ethyl | H | H | none | 1.6 |
| 19 | XX | ethyl | H | H | XXXVII | 2.9 |
| 20 | XX | ethyl | H | H | XXXVIII | 7 |

Examples 21–32 show that treatment of catalyst containing solutions with anhydrous ammonia, an amine resin or a soluble organic amine, improves the extraction efficiency.

Example 21

A mixture comprising predominantly of organic dinitriles and a Ni diphosphite complex, with the diphosphite ligand shown in Structure IX (where R17 is isopropyl, R18 is H, and R19 is methyl) and $ZnCl_2$ (equimolar with nickel) was divided into two portions. One portion was treated with excess ammonia by bubbling anhydrous ammonia through the mixture and the other portion was untreated for comparison. Both ammonia-treated and untreated portions were separately liquid-liquid extracted using cyclohexane in a Karr type column. Catalyst recovery was complete for the ammonia-treated mixture but only 76% recovery was found from the untreated mixture.

Example 22

A mixture comprised predominantly of organic dinitriles and a Ni diphosphite complex, with the diphosphite ligand shown in Structure IX (where R17 is isopropyl, R18 is H, and R19 is methyl) and $ZnCl_2$ (equimolar with nickel) was divided into two portions. One portion was treated by contacting with an equal weight of Amberlyst 21 resin, and the other portion was untreated for comparison. Both resin-treated and untreated portions were separately liquid-liquid batch extracted with an equal weight of cyclohexane. Catalyst recovery was essentially complete for the resin-treated mixture but only 77% recovery was found from the untreated mixture.

Example 23

A mixture comprised predominantly of organic dinitriles and a Ni diphosphite complex, the structure of the diphosphite ligand being shown in Structure XXII (where R17 is methyl, R18 is methyl and R19 is H), and $ZnCl_2$ (equimolar with nickel) was divided into two portions. One portion was treated by contacting with an equal weight of Amberlyst 21 resin, and the other portion was untreated for comparison. Both resin-treated and untreated portions were separately liquid-liquid batch extracted with an equal weight of cyclohexane. Catalyst recovery was 91% for the resin-treated mixture but only 45% recovery was found from the untreated mixture.

Examples 24–35

Use the Following Common Protocol

Catalyst mixtures derived from pentenenitrile hydrocyanation comprised of pentenenitrile and dinitriles (predominantly adiponitrile) in a ratio of about 0.3, a Ni diphosphite catalyst (1.5 wt %), and $ZnCl_2$ (about 0.25 wt %) were divided into three portions and the second and third portion treated either with Amberlyst A-21 resin (1 volume of the Amberlyst A-21® resin to 2 volumes of dinitrile solution), or pyridine and heated at 50° C. An equal weight of cyclohexane was added to each portion, heated to 50° C. and agitated vigorously, and then allowed to settle at 50° C. for about 30 minutes. Samples were carefully withdrawn from top and bottom liquid phases. The top phase being the solvent or extract phase, the bottom being the raffinate phase. Analysis was done for all samples. The results are shown in Table 5.

TABLE 5

Treatment with Amberlyst 21 ® or Pyridine

| Example | Ligand | $R^{17}$ | $R^{18}$ | $R^{19}$ | Additive | Amount wt % | Extraction coefficient |
|---|---|---|---|---|---|---|---|
| 24 | XXIV | methyl | H | H | none | | 0.2 |
| 25 | XXIV | methyl | H | H | Amberlyst 21 ® | | 31 |
| 26 | XXIV | methyl | H | H | pyridine | 9 | 29 |
| 27 | XIII | methyl | H | H | none | | 0.6 |
| 28 | XIII | methyl | H | H | Amberlyst 21 ® | | 12 |
| 29 | XIII | methyl | H | H | pyridine | 5 | 100 |
| 30 | XV | methyl | H | H | none | | 0.4 |
| 31 | XV | methyl | H | H | Amberlyst 21 ® | | 26 |
| 32 | XV | methyl | H | H | pyridine | 3 | 74 |
| 33 | XVII | methyl | H | H | none | | 0.6 |
| 34 | XVII | methyl | H | H | Amberlyst 21 ® | | 7.4 |
| 35 | XVII | methyl | H | H | pyridine | 4 | 10 |

Example 36–43

Use the Same Common Protocol for Treatment with Anhydrous NH₃

Catalyst mixtures derived from pentenenitrile hydrocyanation comprised of pentenenitrile and dinitriles (predominantly adipontrile) in a ratio of about 0.3, a Ni diphosphite catalyst (1–1.5 wt %), and $ZnCl_2$ (about 0.2 wt %) were divided into two portions. One portion was left untreated. The second portion was treated by bubbling $NH_3$ through the solution for 10 minutes, followed by nitrogen to remove any unreacted $NH_3$. An equal weight of cyclohexane was added to each portion and agitated vigorously at room temperature, and then allowed to settle. Samples were carefully withdrawn from top and bottom liquid phases. The top phase being the solvent or extract phase, the bottom being the raffinate phase. Analysis was done for all samples. The results are shown in Table 6.

TABLE 6

Treatment with ammonia

| Example | Ligand | R17 | R18 | R19 | Extract coeff. No treatment | Extract coeff. NH3 Treatment |
|---|---|---|---|---|---|---|
| 36 | XIII | methyl | H | H | 0.6 | 9 |
| 37 | XVI | methyl | H | H | 1.3 | 133 |
| 38 | XV | methyl | H | H | 0.4 | 55 |
| 39 | XI | methyl | H | H | 2 | 7.8 |
| 40 | XIX | methyl | H | H | <~0.1 | 9.7 |
| 41 | XVIII | methyl | H | H | 1 | 21 |
| 42 | XIII | ethyl | H | H | 1.2 | 21 |
| 43 | XIII | ** | ** | ** | 0.9 | 35 |

** 1/3 of R17, R18 and R19 were methyl, the other 2/3 were H. This was done in such a way that only one of the R17, R18 or R19 was methyl for a given aromatic ring.

What is claimed:

1. A process for recovering diphosphite-containing compounds from a mixture comprising diphosphite-containing compounds and organic mononitriles and organic dinitriles, using liquid-liquid extraction, wherein the molar ratio of organic mononitrile present to organic dinitrile is from about 0.65 to about 2.5 and wherein the extraction solvent is a saturated or unsaturated alkane or saturated or unsaturated cycloalkane.

2. A process according to claim 1 wherein the molar ratio of organic mononitrile to organic dinitrile is from about 1.0 to about 1.5.

3. A process for recovering diphosphite-containing compounds from a mixture comprising diphosphite-containing compounds, organic mononitriles and dinitriles, and Lewis acid, using liquid-liquid extraction, wherein the molar ratio of organic mononitrile present to organic dinitrile is from about 0.01 to about 2.5 and wherein the mixture is treated with a Lewis base compound selected from the group consisting of monodentate phosphite ligand alcohol, water, organoamines, ammonia, and, basic resin prior to the liquid extraction, and wherein the solvent is a saturated or unsaturated alkane or saturated or unsaturated cycloalkane.

4. A process according to claim 1, 2, or 3 wherein the diphosphite-containing compound is a Ni complex with a diphosphite ligand selected from the group consisting of:

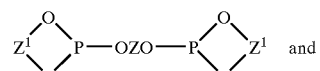

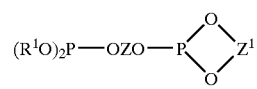

wherein in diphosphite ligand structures I, II, and III, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and wherein Z and $Z^1$ are independently selected from the group consisting of structural formulae IV, V, VI, VII, and VIII:

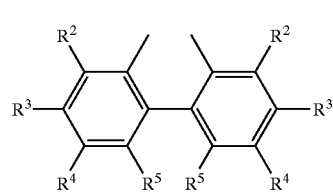

wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;
X is O, S, or $CH(R^{10})$;
$R^{10}$ is H or $C_1$ to $C_{12}$ alkyl;

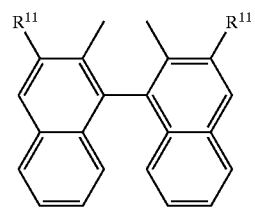

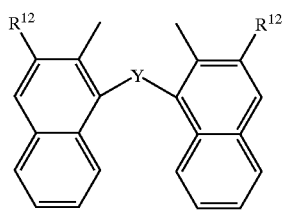

wherein
$R^{11}$ and $R^{12}$ are independently selected from the group consisting of H, $C_1$ to $C_{12}$ alkyl, and $C_1$ to $C_{12}$ alkoxy and $CO_2R^{13}$, $R^{13}$ is $C_1$ to $C_{12}$ alkyl, or $C_6$ to $C_{10}$ aryl unsubstituted or substituted with $C_1$ to $C_4$ alkyl;

Y is O, S, or $CH(R^{14})$;

$R^{14}$ is H or $C_1$ to $C_{12}$ alkyl;

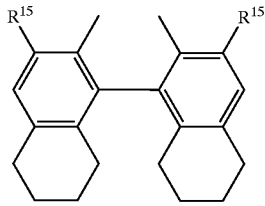

VIII wherein $R^{15}$ is selected from the group consisting of H, $C_1$ to $C_{12}$ alkyl, and $C_1$ to $C_{12}$ alkoxy and $CO_2R^{16}$, $R^{16}$ is $C_1$ to $C_{12}$ alkyl, or $C_6$ to $C_{10}$ aryl, unsubstituted or substituted with $C_1$ to $C_4$ alkyl, and wherein for structural formulae I through VII, the $C_1$ to $C_{12}$ alkyl, and $C_1$ to $C_{12}$ alkoxy groups may be straight chain or branched.

5. A process according to claim 1, 2, or 3 wherein the extraction is carried out above 40° C.

6. A process according to claim 3 wherein the Lewis base compound is selected from the group consisting of water, methanol, ethanol, isopropanol, ethylene glycol, phenol, cresol, or xylenol.

7. A process according to claim 3, wherein the Lewis base compound is a monodentate triarylphosphite wherein the aryl groups are unsubstituted or substituted with alkyl groups having 1 to 12 carbon atoms, and wherein the aryl groups may be interconnected.

8. A process according to claim 3 wherein the Lewis base compound is selected from the group consisting of anhydrous ammonia, pyridine, alkylamine, dialkylamine, and trialkylamine wherein the alkyl groups have 1 to 12 carbon atoms.

9. A process according to claim 3 wherein the Lewis base compound is Amberlyst 21® resin.

10. A process according to claim 1, 2, or 3 wherein the extraction solvent is cyclohexane.

11. A process according to claim 1, 2, or 3 wherein said process is carried out in an extraction column or a mixer-settler.

12. A process according to claim 1, 2, or 3 wherein said process is used in a hydrocyanation process.

* * * * *